United States Patent [19]

Shudo

[11] Patent Number: 4,703,110

[45] Date of Patent: Oct. 27, 1987

[54] BENZOIC ACID DERIVATIVES HAVING A PARA SUBSTITUENT WHICH IS A SUBSTITUTED PHENYL GROUP CONNECTED BY A LINKING RADICAL; USEFUL IN NEOPLASTIC CELL DIFFERENTIATION AND DIAGNOSIS

[75] Inventor: Koichi Shudo, 2-25, 6-102, Higashiyama, Meguroku Tokyo, Japan

[73] Assignee: Koichi Shudo, Tokyo, Japan

[21] Appl. No.: 753,036

[22] Filed: Jul. 8, 1985

[30] Foreign Application Priority Data

Jul. 7, 1984 [JP] Japan ................................ 59-141194
Sep. 19, 1984 [JP] Japan ................................ 59-197089

[51] Int. Cl.$^4$ ...................... C07C 63/06; C07C 69/78; C07C 105/00; C07C 107/06
[52] U.S. Cl. .................................... 534/566; 534/799; 534/851; 534/854; 534/860; 514/150; 514/507; 514/532; 514/534; 514/535; 514/538; 514/539; 514/557; 514/563; 514/568; 514/475; 549/556; 549/557; 560/20; 560/21; 560/51; 562/455; 562/459
[58] Field of Search ............... 534/566, 851, 854, 860, 534/799; 560/51, 20, 21; 549/556, 557; 562/455, 459; 514/150, 532, 557, 568, 475, 507, 534, 563, 535, 538, 539

[56] References Cited

U.S. PATENT DOCUMENTS

| 1,565,229 | 12/1925 | Kalischer et al. | 534/860 X |
| 3,190,876 | 6/1965 | Skoultchi et al. | 534/851 X |
| 4,518,226 | 5/1985 | Shionozaki | 534/566 X |

FOREIGN PATENT DOCUMENTS

| 2854354 | 7/1979 | Fed. Rep. of Germany | 534/566 |
| 25-108230 | 8/1950 | Japan | 534/566 |

OTHER PUBLICATIONS

Baggett et al., Chemical Abstracts, vol. 55, 2594a-g (1961).
Bayer, Chemical Abstracts, vol. 50, 1086a-d (1956).
Berti et al., Chemical Abstracts, vol. 55, 6435d-h (1961).
Hirwe et al., Chemical Abstracts, vol. 37, 4061 2-5 (1943).
Konno et al., Chemical Abstracts, vol. 89, 42807m (1978).
Kunihiro et al. I, Chemical Abstracts, vol. 83, 192859v (1975).
Kunihiro et al. II, Chemical Abstracts, vol. 84, 13502z (1976).
Lukashevich, Chemical Abstracts, vol. 33, 3769 2-5 (1939).
Nisonoff et al., J. Amer. Chem. Soc., vol. 79, pp. 1516 to 1622 (1957).
Nomura et al., Chemical Abstracts, vol. 61, 12115a-c (1964).
Pohloudeu-Fabini et al., Chemical Abstracts, vol. 55, 5870a-c (1961).
Siegler et al., Chemical Abstracts, vol. 38, 6471-6472 (1944).
Tetsuo et al. I, Chemical Abstracts, vol. 82, 120092w (1975).
Tetsuo et al. II, Chemical Abstracts, vol. 84, 43697; (1976).
Woolfolk et al., Chemical Abstracts, vol. 50, 4071f-h (1956).
Zerweck et al., Chemical Abstracts, vol. 49, 10365h,i (1955).
Pawson, et al. Retinoids at the Threshold: Their Biological Significance and Therapeutic Potential, J. Med. Chem. 25, 1269,1277 (1982).
Mayer, et al. Retinoids, a New Class of Compounds with Prophylactic and Therapeutic Activities in Oncology and Dermatology, Experientia 34, 1105-1119.
Koeffler P., Induction of Differentiation of Human Acute Myelogenous Leukemia Cells: Therapeutic Implications, J. Am. Soc. Hematology 62, 709-721 (1983).
Breitman T. R., et al., Induction of Differentiation of the Human Promyelocytic Leukemia Cell Line (HL-60) by Retinoic Acid, Proc. Natl. Acad. Sci. 77, 2936-2940 (1980).
Moon R. C. et al., Inhibition of Carcinogenesis by Retinoids, Cancer Research Suppl 43, 2469s-2475s (1983).

*Primary Examiner*—Floyd D. Higel
*Attorney, Agent, or Firm*—Gordon W. Hueschen

[57] ABSTRACT

The application discloses certain benzoic acid compounds, the same being more adequately described as benzoic acid derivatives having a para substituent which is a substituted phenyl radical attached to the benzoic acid in the para position by any one of a variety of linking groups, representative compounds being p-(3,4-diisopropylphenylcarbamoyl) benzoic acid and p-(5,6,7,8-tetrahydro-5,5,8,8-tetramethyl-2-naphthylcarbamoyl)benzoic acid, pharmaceutical compositions thereof, method of treating therewith, method of diagnosis therewith, and method for the preparation thereof. The compounds and compositions are useful for diagnosis of leukemia types, the treatment of dermatological disorders, and as differentiation-inducing agents for neoplastic cells.

6 Claims, No Drawings

BENZOIC ACID DERIVATIVES HAVING A PARA SUBSTITUENT WHICH IS A SUBSTITUTED PHENYL GROUP CONNECTED BY A LINKING RADICAL; USEFUL IN NEOPLASTIC CELL DIFFERENTIATION AND DIAGNOSIS

BACKGROUND OF THE INVENTION

1. Field of the Invention

Some chondrogenetic disorders and dermatological disorders such as psoriasis and malignant disorders such as leukemia can be looked upon as a disease involving a block or an abnormality in differentiation. The present invention relates to novel organic compounds, which have great potential as useful medicaments and which may accordingly be developed and offered for treating the disorders of humans and animals.

Further, the compounds of the prevent invention can be used for diagnosis of leukemia.

2. Description of the Prior Art

It is already known that an interesting method exists, by which the differentiation is effected and an extinction of cancer cells caused to occur (J. Med. Chem. 25 1269–1277 (1982) with Title: Retinoids at the Threshold: Their Biological Significance and Therapeutic Potential; Cancer Research (Suppl.) 43 2469s–2475s May 1983 with Title: Inhibition of Carcinogenesis by Retinoids; BLOOD of J.A.S. of Hematology 62 709–721 (1983) with Title: Induction of Differentiation of Human Acute Myelogenous Leukemia Cell. Therapeutic Implications; Experientia 34 1105–1246 1978 with Title: Retinoids, a new class of compounds with prophylactic and therapeutic activities in oncology and dermatology and Cell Technology 2, No. 12 (1983)). This literature reports also that retinoic acid, retinoids and related compounds have significant therapeutic potential in oncology and dermatology.

In the specification of DOS No. 28 54 354, it is reported that stilbene derivatives such as p-((E)-2-(5,6,7,8-tetrahydro-5,5,8,8-tetramethyl-2-naphthyl)propenyl)-benzoic acid are pharmacologically valuable and useful for systemic and topical treatment and prophylaxis of benign or malignant tumors. These compounds and retinoids are said to be suitable for systemic and topical treatment of acne, psoriasis and precancerous conditions and of other dermatophathy which is accompanied by a hyperkeratinization as well as other pathologic and allergic dermatological disease.

DETAILED DESCRIPTION OF THE THE INVENTION

It has now been found that the benzoic acids of the formula (I):

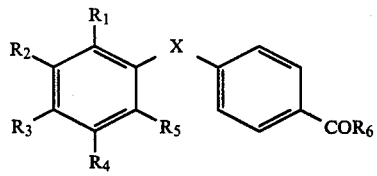

(I)

wherein $R_1$, $R_2$, $R_3$, $R_4$ and $R_5$ may be the same or different, each represents hydrogen, middle and lower alkyl and/or cycloalkyl having 3 to 7 atoms, with the proviso each can not be hydrogen simultaneously, and both neighboring substituents may be combined with each other to form a ring having 5 to 12 carbon atoms, $R_6$ represents hydroxyl, lower alkoxyl, lower alkylamino of the formula $-NR_7'R_8'$, wherein $R_7'$ and $R_8'$ each represent hydrogen or lower alkyl, X represents a group of the formula:

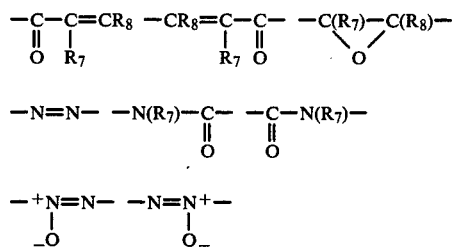

wherein $R_7$ and $R_8$ represent hydrogen or lower alkyl, are capable of inducing the differentiation of premalignant and malignant cells, especially leukemia cells, to morphologically and functionally mature cells which cannot proliferate further, and can therefore be used in the therapy of premalignant and malignant diseases of humans and animals.

By the term "lower" in formula I is meant a straight or branched carbon chain having 1–6 carbon atoms. Therefore, the lower alkyl moiety of the lower alkyl, lower alkoxy, and lower alkylamino group encompassed by $R_1$, $R_2$, $R_3$, $R_4$ and $R_5$ is representatively methyl, ethyl, propyl, isopropyl, butyl, secbutyl, tert-butyl, etc. The lower alkoxy moiety of the lower alkoxy group is representatively methoxy, ethoxy, propoxy, butoxy, etc., and the lower alkylamino group is representatively mono- or dimethylamino, mono- or diethylamino, etc. By cycloalkyl there is representatively intended cyclopropyl, cyclobutyl, cyclopentyl, methylcyclopropyl, cyclohexyl and the like.

When the neighboring substituents combine to form a ring, together with two carbon atoms of phenyl group, the compound can be shown, for example, as following general formula

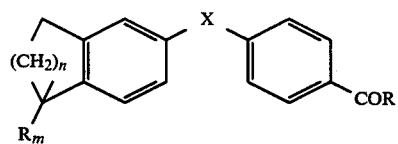

whereby R means a lower alkyl group, n is 1–3 and m is 1–5.

The compounds of above-shown general formula I provided by this invention form salts with bases. This invention includes the pharmaceutically-acceptable salts of the compounds of general formula I, and examples of these salts are the salts with alkali metals such as sodium, potassium, etc., or alkaline earth metals such as calcium, etc.; the salts with ammonia; and the salts with organic bases such as methylamine, ethylamine, diethylamine, trimethylamine, triethylamine, pyridine, picoline, arginine, lysine, etc.

The compounds of this invention have been tested according to established test procedure which shows the differentiation of malignant cells, whereby the differentiation of human acute promyelocytic leukemia cells (HL-60) and their conversion to mature granulocytes (myelocytes) can be assayed by an observation of the morphological changes of nuclei and further by the measurement of the degree of reduction of nitro-blue tetrazolium (NBT) which is induced by a test compound (Proc. Natl. Acad. Sci. USA 77, 2936–2940 (1980) with Title: Induction of differentiation of the human promyelocytic leukemia cell line (HL-60) by retinoic acid).

The HL-60 cells are cultured in plastic flasks in RPMI-1640 medium supplemented with 5% heat inactivated fetal calf serum and antibiotics (penicillin G and streptomycin). The cells ($3 \times 10^4$ /ml) were cultured with a compound of the present invention for 4 days. Growth inhibition of the cells by the test compounds was determined by counting the number of cells by microscope and relative ratio was examined by taking the number of cells by control (without test compound) as 100%. The cells are fixed and stained with Wright-Giemsa to examine the morphological changes of the nuclei.

The cells treated with the present compounds are differentiated to mature granulocytes (myelocytes, metamyelocytes and neutrophiles), just as the cells treated with retinoic acid.

The biochemical activity of cells treated with the compound was measured as follows:

The cells after 5 days incubation are centrifuged and diluted with RPMI-1640 medium supplemented with 5% fetal calf serum, to provide a definite number of the cells. To the diluted cell suspension are then added 200 ng/ml of 12-O-tetradodecanoylphorbol-13-acetate (TPA) and the resulting culture medium is then incubated for 20 minutes at 37° C. in the presence of 0.1% of NBT. Thus, the mature differentiated cells containing blue-black formazan is counted by microscopy, so that the ratio of the cells having the ability to reduce NBT, to total cells, can be calculated.

The cells treated with the compound of this invention show the NBT reduction activity which corresponds to the important biochemical activity of differentiated cells.

The results of the tests according to the above mentioned methods are summarized in Table 1.

As can be seen from the results shown in Table 2 the activity of the compounds of this invention is observed at a concentration less than $10^{-6}$ Mol.

The alkyl-substitution $R_1$, $R_2$, $R_3$, $R_4$ and $R_5$ on the phenyl group in the formula (I) is a characteristic of the benzoic acids and their derivatives which are the compounds of this invention. Such a compound, wherein the alkyl group is a middle alkyl group, especially wherein one alkyl substituent is an isopropyl, cyclopropyl, cyclobutyl, or butyl group, or wherein two or more substituents are ethyl, isopropyl or tert-butyl group, is effective. On the other hand such a compound, wherein all of $R_1$–$R_5$ are hydrogen, does not exhibit the desired activity.

The most important alkyl substituents are $R_2$, $R_3$ and $R_4$. The compounds, wherein two alkyl substituents $R_2$ and $R_3$ are combined to form a ring, are most important.

The compounds of the formula (I), wherein $R_7$ and $R_8$ represent hydrogen or methyl are especially effective. The most important —X-group are

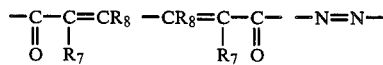

-continued

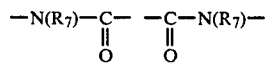

Several compounds of the formula (I), wherein X means, $SO_2NH$—, —O.CO—, —COO—, —NHCONH—, —NHCOO— and —O.SO$_2$ — as equivalent substituents, have been synthesized and tested.

These compounds can be used as diagnosis for determining the type of leukemia by a measuring method, whereby the blood of a patient with leukemia is incubated in vitro in the presence of a present compound in an analogous manner as described in the morphological assay for the HL-60 cells: Only promyelocytic leukemia cells, but no lymphocytic leukemia cells, differentiate to mature granulocytes, which can be clearly determined by microscope (See: Saibo (Cells) 14, 533 (1982)).

When the incubation is performed in a soft agar, promyelocytic leukemia cells do not form a colony, since the differentiated cells do not proliferate further.

Thus, these compounds are very useful in the determination of promyelocytic leukemia, which enables to select the therapeutical methods.

At the same time the compounds of this invention are very useful as reagents for research of leukemia.

A test of treatment of nude mice, to which HL-60 have been transplanted, with a compound of the present invention is performed as follows:

A test compound (e.g., p-(5,6,7,8-tetrahydro-5,5,8,8-tetramethyl-2-naphthylcarbamoyl)benzoic acid) is suspended in 10% (v/v) Tween 80 in a concentration of 10 mg/ml. Cells ($5 \times 10^7$) of HL-60 were transplanted subcutaneously to a nude mouse (BALB/c, nu/nu female Nihon Clea).

At the end of days 9, 14 and 17 after the transplantation, 0.1 ml of the suspension per 10 g of body weight of mouse were administrated per os two times at intervals of 7 hours (200 mg/kg/day). Tumor volume measurements after 4, 6, 8 and 11 days after the first administration show that tumor growth was clearly suppressed; The increased of tumor volume of the treated mice are $1/5$–$\frac{1}{2}$ compared with the untreated mice.

Since the compounds of the present invention differentiate the leukemia cells to mature granulocytes morphologically and functionally and inhibit the cell-growth potentially, they can be used as medicine for treatment of humans and animals with cancer.

Thus, it was demonstrated that the compounds of the present invention have remarkable anticancer-antileukemic activity, when tested on nude mice transplanted with human-derived leukemia cells. These facts also suggest that the compounds of this invention are effective against neuroblastoma, squamous cell carcinoma, and melanoma.

These compounds suppress the hyperkera keratinization of human tissue cells, and are useful for the treatment of cystic acne, psoriasis and related cutaneous disorders of keratinization and of epithelial differentiation.

The medical compositions containing the compounds of their invention as the main component are formulated in a conventional manner using conventional carriers for formulation and excipients. The medicaments may be administered orally as tablets, pills, capsules, granules, etc., or may be administered parenterally as injections such as intravenous injections, intramuscular injections etc., in the form of ointments, creams and the like for external application, in particular for the treatment of dermatological disorders. They may be used as aerosols, suppositories, etc. The doses of the medicaments are properly determined according to each case on considering the symptom, the age of patient, sex distinction, etc., but are usually 1-300 mg per day for an adult in case of oral administration and 1-100 mg per day for an adult in case of parenteral administration, the daily amount usually being administered in 2-3 separate dosages.

The compounds represented by the formula (I) can be prepared by the following method:

(a) a compound represented by the formula (I), wherein X represents a group of the formula —CO—C($R_7$)=C$R_8$—, is prepared by condensation of a corresponding acetophenone derivative with a terephthalaldehyde acid ester or a derivative in the presence of a base, (b) a compound represented by the formula (I), wherein X represents a group of the formula:

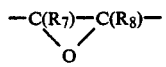

is prepared by oxidation of a corresponding compound, wherein X represents a group of the formula:

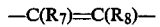

with a reagent for epoxidation, (c) a compound represented by the formula (I), wherein X represents a group of the formula —N=N—, is prepared by condensation of a corresponding aniline derivative with a p-nitroso-benzoic acid in the presence or absence of an acidic catalyst, (d) a compound represented by the formula (I), wherein X represents a group of the formula —N(O)=N— or —N=N(O)—, is prepared by condensation of a corresponding phenylhydroxylamine with a p-nitro-benzoic acid or a derivative, as described in item (c), (e) a compound represented by the formula (I), wherein X represents a group of the formula —N=N(O)— or —N(O)=N—, is prepared by condensation of a nitrosobenzene derivative with a p-hydroxyl-amino benzoic acid or a derivative thereof, as described in item (c), (f) a compound represented by the formula (I), wherein X represents a group of the formula —N($R_7$)—CO—, is prepared by acylation of a corresponding aniline derivative with a functional derivative of terephthalic acid (acid halogenide or ester of the acid), and (g) a compound represented by the formula (I), wherein X represents a group of the formula —CO—N($R_7$)—, is prepared by acylation of a p-amino benzoic acid or a derivative thereof with a functional derivative of a corresponding benzoic acid in the usual manner and, if necessary or desirable, the thus obtained compound is hydrolized.

The following examples are given by way of illustration only and are not to be construed as limitations of this invention.

EXAMPLE 1

To a solution of 176 mg (1 mmole) of p-tert.-butyl acetophenone and 164 mg (1 mmole) of terephthalic aldehyde acid methyl ester in 8 ml of ethanol was added 10 ml of 1N sodium hydroxide and the reaction mixture was stirred at room temperature for one night. After completion of the reaction, the reaction solution was acidified with dil. hydrochloric acid followed by extraction with ethyl acetate. The extracted solution was washed with water until the pH of the washing became 7 and dried over anhydrous sodium sulfate.

After removing the solvent by distillation, the objective compound of the formula (I), wherein $R_3$ means t-butyl: X means a group of the formula: —COCH=CH— and $R_6$ means hydroxyl group, and $R_1$, $R_2$, $R_4$ and $R_5$ are hydrogen having a melting point of 245°-246° C. were obtained. (yield; 75.2%)

Elemental Analysis for $C_{20}H_{20}O_3$: Calcd. (%): C; 77.90, H; 6.54; Found (%): C; 77.62, H; 6.43.

To a solution of the thus obtained carboxylic acid in methanol was added a solution of diazomethane in either to obtain quantitatively the methyl ester having a melting point of 119°-120.5° C.

EXAMPLE 2

A solution of 100 mg (0.287 mmole) per p-(E)-2-(5,6,7,8-tetrahydro-5,5,8,8-tetramethyl-2-naphthyl)ethenyl benzoic acid methyl ester in 5 ml of chloroform was added to a solution of 50 mg (0.289 mmole) of m-chloroperoxybenzoic acid in chloroform and the mixture was refluxed for two hours. After disappearance of the raw materials, the reaction solution was cooled and the insoluble materials were removed with filtration. The solution was washed successively with 1N aq. sodium carbonate solution, 1N aq. sodium bicarbonate solution and saturated aq. saline solution. It was dried over anhydrous sodium sulfate. The distillation of the solvent gave an epoxy compound represented by the formula (I), wherein $R_2$ and $R_3$ mean a group of the formula: —C(CH$_3$)$_2$CH$_2$CH$_2$C(CH$_3$)$_2$— and X means a group of the formula:

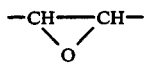

and $R_6$ means methoxy, and $R_1$, $R_4$ and $R_5$ are hydrogen, which has a melting point of 163°-166° C. (yield; 92.0%)

After hydrolysis of the epoxy compound (ester) thus obtained with 1N solution of sodium hydroxide in ethanol and neutralization with hydrochloric acid, the resulting solution was extracted with ethyl acetate The solvent was removed by distillation and the residue was recrystallized from ethyl acetate to obtain the corresponding carboxylic acid having a melting point of 215°-216° C.

Elemental Analysis for $C_{23}H_{26}O_3$: Calcd. (%): C; 78.82, H; 7.48; Found (%): C; 79.03, H; 7.74.

EXAMPLE 3

The nitration of 1.2 g of 5,5,8,8-tetramethyl-5,6,7,8-tetrahydronaphthalene with nitric acid/sulfuric acid mixture in sulfuric acid gave a 2-nitro derivative having a melting point of 71°-72° C. (0.9 g, recrystallized from methanol). The reduction of the obtained nitro derivative with Pd-C as catalyst in alcohol gave 2-amino-5,6,7,8-tetrahydro-5,5,8,8-tetramethyl-naphthalene having a melting point of 72°-73° C. (recrystallized from hexane).

To a solution of 0.2 g of the thus obtained amino compound in 10 ml of acetic acid was added 0.1 of trichloroacetic acid and the solution was mixed with a slight excess of 4-nitroso benzoic acid methyl ester and allowed to stand at room temperature for two hours. The solvent was removed by distillation and the resulting product was recrystallized from methanol to yield 0.32 g of the azo-compound of the formula (I), wherein $R_2$ and $R_3$ mean a group of the formula: —$C(CH_3)_2CH_2CH_2C(CH_3)_2$—, $R_6$ means methoxy and X means a group of the formula: —N=N—, and $R_1$, $R_4$ and $R_5$ are hydrogen, which has a melting point of 118.5°–119.5° C.

Elemental Analysis for $C_{22}H_{26}N_2O_2$: Calcd. (%): C; 75.40, H; 7.48, N; 7.99; Found (%): C; 75.28, H; 7.29, N; 7.81.

A hydrolysis of the thus obtained azo-compound in methanol with 1N sodium hydroxide and the treatment described in Example 2 gave the corresponding carboxylic acid having a melting point of 287°–288° C.

EXAMPLE 4

100 mg of nitro-compound obtained in Example 3 dissolved in 30 ml of wet tetrahydrofuran was reduced with aluminum amalgam (prepared from 300 mg of aluminum foil and 30 of 5% aqueous solution of $HgCl_2$) to yield the corresponding hydroxylamine derivative, which was, without purification, reacted with a slight excess of p-nitroso benzoic acid methyl ester to give an azoxy derivatve having the formula (I): wherein $R_2$ and $R_3$ mean a group shown by the formula: —$C(CH_3)_2CH_2CH_2C(CH_3)_2$—, $R_6$ means methoxy and X is a group of the formula: —N=(O)—, and $R_1$, $R_4$ and $R_5$ are hydrogen, having a melting point of 114°–115° C. (recrystallized from hexane). MASS: M+ = 366.

EXAMPLE 5

1 mmole of 2-amino-5,6,7,8-tetrahydro-5,5,8,8-tetramethyl naphthalene obtained in Example 3 was reacted with 1.1 mmole of terephthalic acid chloride monomethyl ester in pyridine at room temperature to quantitatively obtain a compound of the formula (I), wherein $R_2$ and $R_3$ means a group of the formula: —$C(CH_3)_2CH_2CH_2$—$C(CH_3)_2$—, X means a group of the formula —NH—CO— and $R_6$ means methoxy, and $R_1$, $R_4$ and $R_5$ are hydrogen, which was recrystallized from methylene chloride/hexane.

m.p. 211°–212° C.

A solution of the thus obtained compound in methanol was reacted with 1N sodium hydroxide for two hours at room temperature, whereafter the solution was neutralized with dilute hydrochloric acid and extracted with ethyl acetate.

The solvent was removed by distillation to give crystals. A recrystallization of the crystals from ethyl acetate/hexane gave a terephthalic acid amide derivative of the formula (I), wherein $R_2$ and $R_3$ mean a group of the formula: —$C(CH_3)_3CH_2CH_2C(CH_3)_2$—, X means a group of the formula: —NH—CO— and $R_6$ means hydroxyl, and $R_1$, $R_4$ and $R_5$ are hydrogen.

m.p. 205.5°–206.5° C.

The acid was converted in the usual manner to the ammonium salt having a melting point of 145°–146° C.

EXAMPLE 6

1.1 mmole of 3,4-diethyl benzoic acid chloride was reacted with 1 mmole of 4-amino benzoic acid methyl ester in 10 ml of anhydrous pyridine for five hours at room temperature. After addition of water, the reaction solution was extracted with chloroform, and the extract was washed with dilute hydrochloric acid and water. After removing the solvent by distillation, the resulting residue was recrystallized from methanol to obtain a compound represented by formula (I), wherein $R_2$ and $R_3$ each mean an ethyl group, X means a group having the formula —CO—NH— and $R_6$ means a methoxy group, and $R_1$, $R_4$ and $R_5$ are hydrogen, having a melting point of 162°–165° C. The yield was quantitative.

A number of compounds were synthesized by the same methods. The compounds of No. 1 to 68 (including the compounds obtained in the above Examples) are surmmarized in Table I.

TABLE 1

| | Compound | | | | | | $ED_{50}(m)$ (moles/ liter) | Promyelocytes (%) | Myelocytes and Metamyelocytes (%) | Banded and Segmented Neutrophils (%) | Reductivity of NBT (%) | Growth inhibition Of cells (%) |
|---|---|---|---|---|---|---|---|---|---|---|---|---|
| $R_1$ | $R_2$ | $R_3$ | $R_4$ | $R_5$ | $R_6$ | X | | | | | | |
| | | | Blank | | | | — | 98 | 2 | 0 | 1 | 100 |
| H | H | tBu | H | H | OH | —C(=O)—CH=CH— | $10^{-9}$ | 46 | 48 | 6 | 68 | 7 |
| H | Et | Et | H | H | $OCH_3$ | " | $10^{-8}$ | 38 | 54 | 8 | 72 | 20 |
| H | —(CH$_3$)$_2$CCH$_2$ —(CH$_3$)$_2$CCH$_2$ | | H | H | OH | " | $10^{-10}$ | 2 | 86 | 12 | 95 | 11 |
| H | " | | H | H | $OCH_3$ | " | $10^{-9}$ | 5 | 91 | 4 | 97 | 10 |
| H | tBu | H | tBu | H | OH | " | $10^{-10}$ | 2 | 82 | 16 | 95 | 5 |
| H | tBu | H | H | H | $OCH_3$ | —CH—CH— (epoxide) | $10^{-8}$ | 20 | 69 | 9 | 70 | 20 |
| H | —(CH$_3$)$_2$CCH$_2$ —(CH$_3$)$_2$CCH$_2$ | | H | H | $OCH_3$ | " | $10^{-8}$ | 19 | 63 | 18 | 78 | 18 |
| " | " | " | " | " | " | —C(CH$_3$)—CH— (epoxide) | $10^{-8}$ | 12 | 79 | 9 | 81 | 18 |

TABLE 1-continued

| Compound | | | | | | | $ED_{50}(m)$ (moles/liter) | Promyelocytes (%) | Myelocytes and Metamyelocytes (%) | Banded and Segmented Neutrophils (%) | Reductivity of NBT (%) | Growth inhibition Of cells (%) |
|---|---|---|---|---|---|---|---|---|---|---|---|---|
| $R_1$ | $R_2$ | $R_3$ | $R_4$ | $R_5$ | $R_6$ | X | | | | | | |
| " | " | " | " | " | " | —N=N— | $10^{-9}$ | 41 | 49 | 10 | 60 | 12 |
| H | i-Pr | i-Pr | H | H | OH | " | $10^{-8}$ | 39 | 50 | 11 | 55 | 21 |
| H | —(CH$_3$)$_2$CCH$_2$<br>—(CH$_3$)$_2$CCH$_2$ | | H | H | OH | —N$^+$=N—<br>       $\|$<br>       O$^-$ | $10^{-8}$ | 40 | 53 | 7 | 70 | 17 |
| " | " | " | " | " | " | —NH—CO— | $10^{-10}$ | 3 | 78 | 19 | 98 | 6 |
| " | " | " | " | " | OCH$_3$ | " | $10^{-9}$ | 3 | 85 | 12 | 97 | 10 |
| H | i-Pr | i-Pr | H | H | OH | " | $10^{-8}$ | 7 | 82 | 11 | 90 | 21 |
| Retinoic acid | | | | | | | $10^{-7}$ | 25 | 71 | 4 | 75 | 32 |

TABLE 2

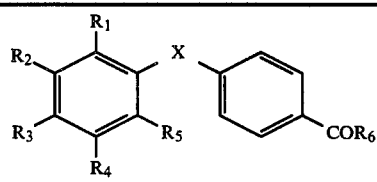

| No. | $R_1$ | $R_2$ | $R_3$ | $R_4$ | $R_5$ | $R_6$ | X | Anal | mp | synthesis |
|---|---|---|---|---|---|---|---|---|---|---|
| 1 | H | —(CH$_3$)$_2$CCH$_2$<br>—(CH$_3$)$_2$CCH$_2$ | | H | H | OH | —C(CH$_3$)—CH—(O) (epoxide) | $C_{24}H_{28}O_3$ | 202.5–203.5 | b |
| 2 | H | " | | H | H | OCH$_3$ | " | $C_{25}H_{30}O_3$ | 137.5–139 | b |
| 3 | H | i-Pr | i-Pr | H | H | OCH$_3$ | " | $C_{23}H_{28}O_3$ | 112–113 | b |
| 4 | H | Et | Et | H | H | OH | " | $C_{20}H_{22}O_3$ | 146–148 | b |
| 5 | H | Et | Et | H | H | OH | —C(=O)—CH=CH— | $C_{20}H_{20}O_3$ | 178.5–180 | a |
| 6 | H | i-Pr | i-Pr | H | H | OH | " | $C_{22}H_{24}O_3$ | 197.5–199 | a |
| 7 | tBu | H | H | tBu | H | OH | " | $C_{24}H_{28}O_3$ | 215–216 | a |
| 8 | H | tBu | H | tBu | H | OH | " | $C_{24}H_{28}O_3$ | 202–203.5 | a |
| 9 | H | H | tBu | H | H | OH | " | $C_{20}H_{20}O_3$ | 245–246 | a |
| 10 | " | " | " | " | " | OCH$_3$ | " | $C_{21}H_{22}O_3$ | 119–120.5 | a |
| 11 | H | —(CH$_3$)$_2$CCH$_2$<br>—(CH$_3$)$_2$CCH$_2$ | | H | H | OH | " | $C_{24}H_{26}O_3$ | 203–204 | a |
| 12 | " | " | | " | " | O—n-Bu | " | $C_{28}H_{34}O_3$ | 128–129.5 | a |
| 13 | " | " | | " | " | OCH$_3$ | " | $C_{25}H_{28}O_3$ | 93.5–94 | a |
| 14 | " | " | | " | " | NH$_2$ | " | $C_{24}H_{27}O_2N$ | 208.5–209 | a |
| 15 | H | Et | Et | H | H | OH | —NH—C(=O)— | $C_{18}H_{19}NO_3 \cdot \frac{1}{2}H_2O$ | 259.5–260.5 | f |
| 16 | H | H | i-Pr | H | H | OH | " | $C_{17}H_{17}NO_3$ | >300 | f |
| 17 | H | i-Pr | H | H | H | OH | " | $C_{17}H_{17}NO_3$ | 103.5–105 | f |
| 18 | " | " | " | " | " | OCH$_3$ | " | $C_{18}H_{19}NO_3$ | 104–106 | f |
| 19 | i-Pr | H | H | H | H | OH | " | $C_{17}H_{17}NO_3$ | 269.5–271 | f |
| 20 | " | " | " | " | " | OCH$_3$ | " | $C_{18}H_{19}NO_3$ | 165.5–167.5 | f |
| 21 | H | tBu | H | H | H | OH | " | $C_{18}H_{19}NO_3$ | Amorph | f |
| 22 | i-Pr | H | H | H | i-Pr | OH | " | $C_{20}H_{23}NO_3 \cdot \frac{1}{2}H_2O$ | >300 | f |
| 23 | " | " | " | " | " | OCH$_3$ | " | $C_{21}H_{25}NO_3$ | 292–293 | f |
| 24 | i-Pr | H | H | i-Pr | H | OH | " | $C_{20}H_{23}NO_3$ | 230–231.5 | f |
| 25 | " | " | " | " | " | OCH$_3$ | " | $C_{21}H_{25}NO_3$ | 183–184.5 | f |
| 26 | i-Pr | H | i-Pr | H | H | OH | " | $C_{20}H_{23}NO_3 \cdot \frac{1}{2}H_2O$ | 244.5–246 | f |
| 27 | " | " | " | " | " | OCH$_3$ | " | $C_{21}H_{25}NO_3$ | 165–166.5 | f |
| 28 | H | i-Pr | H | i-Pr | H | OH | " | $C_{20}H_{23}NO_3$ | 256.5–258.5 | f |
| 29 | " | " | " | " | " | OCH$_3$ | " | $C_{21}H_{25}NO_3$ | 151–152 | f |
| 30 | H | i-Pr | i-Pr | H | H | OH | " | $C_{20}H_{23}NO_3$ | 220.5–221.5 | f |
| 31 | " | " | " | " | " | OCH$_3$ | " | $C_{21}H_{25}NO_3$ | 137.5–138 | f |
| 32 | H | cyclohexyl | H | H | H | OH | —NH—C(=O)— | $C_{20}H_{21}NO_3$ | 237–237.5 | f |
| 33 | " | " | " | " | " | OCH$_3$ | " | $C_{21}H_{23}NO_3$ | 157–158 | f |

TABLE 2-continued

Structure: R1, R2, R3, R4, R5 substituted benzene ring connected via X to a para-COR6 phenyl ring

| No. | R1 | R2 | R3 | R4 | R5 | R6 | X | Anal | mp | synthesis |
|---|---|---|---|---|---|---|---|---|---|---|
| 34 | H | —(CH₃)₂CCH₂—(CH₃)₂CCH₂ | | H | H | OCH₃ | " | C₂₃H₂₇NO₃ | 211–212 | f |
| 35 | H | " | | " | H | OH | " | C₂₂H₂₅NO₃ | 205.5–206.5 | f |
| 36 | H | Et | Et | H | H | OCH₃ | " | C₁₉H₂₁NO₃ | 122–123 | f |
| 37 | H | H | tBu | H | H | OCH₃ | " | C₁₉H₂₁NO₃ | 182–183 | f |
| 38 | " | " | i-Pr | " | " | " | " | C₁₈H₁₉NO₃ | 200–202 | f |
| 39 | H | tBu | H | H | H | " | " | C₁₉H₂₁NO₃ | 143.5–145 | f |
| 40 | " | C₅H₉ | " | " | " | " | " | C₂₀H₂₁NO₃ | Amorph | f |
| 41 | H | Et | H | H | H | OH | —N=N— | C₁₅H₁₄N₂O₂ | 191.5–192 | c |
| 42 | H | H | i-Pr | H | H | OH | " | C₁₆H₁₆N₂O₂ | 266.5–268.5 | c |
| 43 | H | i-Pr | H | H | H | OH | " | C₁₆H₁₆N₂O₂ | 186.5–188.5 | c |
| 44 | i-Pr | H | H | H | H | OH | " | C₁₆H₁₆N₂O₂ | 195.5–197 | c |
| 45 | H | tBu | H | H | H | OH | " | C₁₇H₁₈N₂O₂ | 245–146 | c |
| 46 | i-Pr | H | H | H | i-Pr | OH | " | C₁₉H₂₂N₂O₂ | Amorph | c |
| 47 | i-Pr | H | H | i-Pr | H | OH | " | C₁₉H₂₂N₂O₂ | 192.5–193 | c |
| 48 | i-Pr | H | i-Pr | H | H | OH | " | C₁₉H₂₂N₂O₂ | 206–208 | c |
| 49 | H | i-Pr | H | i-Pr | H | OH | " | C₁₉H₂₂N₂O₂ | 201–203 | c |
| 50 | H | i-Pr | i-Pr | H | H | OH | " | C₁₉H₂₂N₂O₂ | 230.5–232 | c |
| 51 | H | cyclo-hexyl | H | H | H | OH | " | C₁₉H₂₀N₂O₂ | 248–248.5 | c |
| 52 | H | CH₃ | H | H | H | OCH₃ | " | C₁₅H₁₄N₂O₂ | 115–116.5 | c |
| 53 | " | " | " | " | " | OH | " | C₁₄H₁₂N₂O₂ | 191–193.5 | c |
| 54 | H | H | i-Pr | H | H | OCH₃ | " | C₁₇H₁₈N₂O₂ | 91.5–92 | c |
| 55 | H | Et | Et | H | H | OCH₃ | " | C₁₈H₂₀N₂O₂ | 44–44.5 | c |
| 56 | " | " | " | " | " | OH | " | C₁₇H₁₈N₂O₂ | 215–216 | c |
| 57 | H | —(CH₃)₂CCH₂—(CH₃)₂CCH₂ | | H | H | OCH₃ | " | C₂₂H₂₆N₂O₂ | 118.5–119.5 | c |
| 58 | " | " | | " | " | OH | " | C₂₁H₂₄N₂O₂ | 287–288 | c |
| 59 | H | tBu | H | H | H | OCH₃ | " | C₁₈H₂₀N₂O₂ | 104–105 | c |
| 60 | H | —(CH₃)₂CCH₂—(CH₃)₂CCH₂ | | H | H | OCH₃ | —C(H)—CH— (epoxide, O) | C₂₄H₂₈O₃ | 163–166° | b |
| 61 | " | " | | " | " | OH | " | C₂₃H₂₆O₃ | 215–216 | b |
| 62 | H | tBu | H | H | H | OH | " | C₁₉H₂₀O₃·1/6H₂O | 199–200.5 | b |
| 63 | H | —(CH₃)₂CCH₂—(CH₃)₂CCH₂ | | H | H | OCH₃ | —N⁺(O⁻)=N— | C₂₂H₂₆N₂O₃ | 114–115 | d,e |
| 64 | H | " | | H | H | OCH₃ | —N(CH₃)—CO— | C₂₄H₂₉NO₃ | 117–118 | f |
| 65 | H | Et | Et | H | H | OCH₃ | —CO—NH— | C₁₉H₂₁NO₃ | 162–165 | g |
| 66 | H | H | tBu | H | H | OH | —CH—CH— (epoxide, O) | C₁₉H₂₀O₃ | 207–207.5 | b |
| 67 | H | —(CH₃)₂CCH₂—(CH₃)₂CCH₂ | | H | H | OCH₃ | —CO—NH— | C₂₃H₂₇NO₃ | 206–207 | g |
| 68 | H | " | | H | H | OH | " | C₂₂H₂₅NO₃ | 265–267 | g |

What is claimed is:

1. A benzoic acid derivative represented by a formula selected from the group consisting of

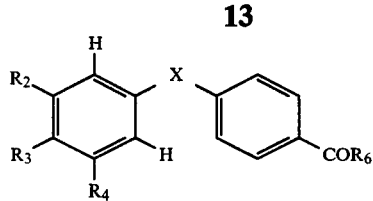

and

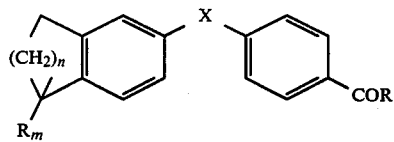

wherein R means a lower-alkyl group, n is 1–3, and m is 1–5, and wherein $R_2$, $R_3$ and $R_4$ are the same or different and each represents hydrogen or middle alkyl of $C_3$–$C_7$ or cycloalkyl having 3–7 atoms, with the proviso that only one can be hydrogen at one time, $R_6$ represents hydroxyl, lower-alkoxyl, a group of the formula —$NR_7'R_8'$, wherein $R_7'$ and $R_8'$ each represents hydrogen or lower alkyl, and X represents a group of the formula

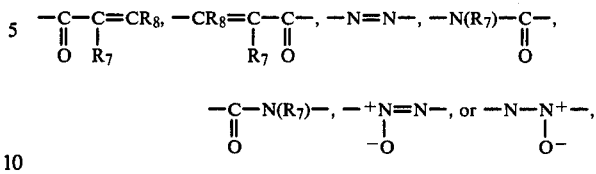

wherein $R_7$ and $R_8$ represent hydrogen or lower-alkyl.

2. A compound of claim 1 which is p-(5,6,7,8-tetrahydro-5,5,8,8-tetramethyl-2-naphthylcarbamoyl)benzoic acid.

3. A compound of claim 1 which is 3',5'-Di-tert-butyl-4-carboxychalcone.

4. A compound of claim 1 which is p-(5,6,7,8-tetrahydro-5,5,8,8-tetramethyl-2-naphthalene carboxyamid)benzoic acid.

5. A compound of claim 1 which is Methyl p-(5,6,7,8-tetrahydro-5,5,8,8-tetramethyl-2-naphthyl)azobenzoate.

6. A compound of claim 1 which is p-(3,4-diisopropylphenylcarbamoyl)benzoic acid.

* * * * *

UNITED STATES PATENT AND TRADEMARK OFFICE
CERTIFICATE OF CORRECTION

PATENT NO. : 4,703,110
DATED : October 27, 1987
INVENTOR(S) : Koichi Shudo

It is certified that error appears in the above-identified patent and that said Letters Patent is hereby corrected as shown below:

Title Page, [56] References Cited, FOREIGN PATENT DOCUMENTS, line 2;
  "25-108230" should read -- 50-108230 -- (Notice of References Cited, attachment to paper 8, dated 5/8/86 - also see original document)
Col. 2, lines 66 & 67; "granuloctyes" should read -- granulocytes --
Col. 6, lines 15 & 16; "either" should read -- ether --
Col. 6, line 20; "mmole) per p-(E)-2-" should read -- mmole) of p-(E)-2- --
Col. 6, line 67; "0.1 of" should read -- 0.1 g of --
Col. 7, line 23; "30 of" should read -- 30 ml of --
Col. 7, line 30; "—N=(O)—," should read -- —N=N(O)—, --
Cols. 9 & 10, Table 2, No. 24, last column labeled "synthesis"; is left blank, should read -- f --
Cols. 11 & 12, Table 2-continued, No. 45, second to last column labeled "mp"; "245-146" should read -- 245-246 --

Signed and Sealed this

Fifteenth Day of March, 1988

Attest:

DONALD J. QUIGG

*Attesting Officer*     *Commissioner of Patents and Trademarks*